United States Patent [19]

Chu et al.

[11] Patent Number: 5,665,889
[45] Date of Patent: Sep. 9, 1997

[54] METHOD FOR THE PRODUCTION OF N-VINYL-2-PYRROLIDONE BY VINYLATION

[75] Inventors: Shiao-Jung Chu; Pine-Sci Kuo; Chu-Chang Dai, all of Hsinchu Hsien; Hsi-Yen Hsu, Taipei; Ching-Tang Lin, Hsinchu, all of Taiwan

[73] Assignee: Industrial Technology Research Institute, Hsinchu, Taiwan

[21] Appl. No.: 589,517

[22] Filed: Jan. 22, 1996

[51] Int. Cl.$^6$ .................................. C07D 207/263
[52] U.S. Cl. ................................ 548/543; 548/552
[58] Field of Search .............................. 548/552, 543

[56] References Cited

U.S. PATENT DOCUMENTS 4,410,726  10/1983  Parthasarathy et al. ............... 548/543
4,873,336  10/1989  Liu et al. ............................... 548/543
5,461,159  10/1995  Huckestein et al. ................... 548/543

*Primary Examiner*—Jacqueline Haley
*Attorney, Agent, or Firm*—W. Wayne Liauh

[57] ABSTRACT

The present invention relates to a method for the production of N-vinyl-2-pyrrolidone with high selectivity. The method is characterized in subjecting 2-pyrrolidone and acetylene to vinylation by using hydroxy end-capped ether oligomers having a molecular weight less than 1000 or linear diols having at least 4 carbon atoms as co-catalysts under the catalyzation of alkali metal salts. At a vinylation temperature of 100°–200° C., a reaction pressure of 7.5–30 atm and a reaction time period of 3–20 hours, N-vinyl-2-pyrrolidones are obtained with yields above 90%.

9 Claims, No Drawings

METHOD FOR THE PRODUCTION OF N-VINYL-2-PYRROLIDONE BY VINYLATION

BACKGROUND OF THE INVENTION

The present invention relates to an improved method for the production of N-vinyl-2-pyrrolidone (NVP). The method uses hydroxy end-capped ether oligomers having a molecular weight less than 1000 or linear diols having more than 4 carbon atoms as co-catalysts for increasing the activity of alkali metal salt catalysts in order to accelerate the vinylation of 2-pyrrolidone with acetylene and obtain a higher yield of N-vinyl-2-pyrrolidone (NVP).

NVP is a valuable and useful compound. Due to its unique physical properties such as water solubility, high polarity, nontoxicity, chemical stability, and cation activity, it has been widely applied in the manufacture of adhesives, paints, textiles, foods and personal medicines. The homopolymers or copolymers thereof have improved film strength, dye compatability, rigity and adhesion.

A conventional method for making NVP is the "Reppe Reaction" which uses 2-pyrrolidone and acetylene as raw materials, and alkali metal salts as catalysts(Brit. Patent No. 1,045,627, U.S.S.R. U.S. Pat. No. 198,339, and Japanese Patent No. 71,09,458). According to the method, NVP is prepared by vinylation in an autoclave at 170° C. and under low pressure or atmospheric pressure. The Reppe method has the disadvantages of low yield and the formation of nonvolatile polymer residues, making the separation and recovery of the desired product difficult. In order to eliminate the disadvantages, BASF and GAF company adopt a two-stage method to produce NVP (CHEM SYSTEM Report,89S9). According to their method, raw material, 2-pyrrolidone (2-p) is first reacted with KOH serving as precursor catalyst to produce a potassium salt catalyst and water. To avoid production of any by-product, potassium 4-amino-butyrate, water must be removed in this stage, and thus the reaction must be operated under vacuum and purged by $N_2$ in batch reactors. After the water is removed completely, the potassium salt catalyst is then reacted with acetylene by vinylation to produce NVP. The whole reaction is depicted in the following reaction scheme:

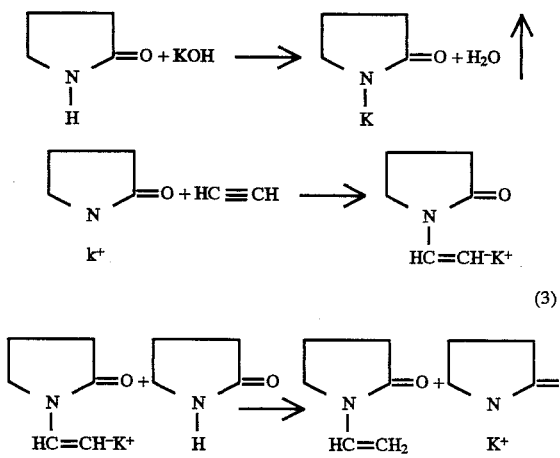

The disadvantage of this method is that the formed water must be removed continuously, otherwise in step (1) the reaction will readily reach an equilibrium state and will not proceed to the right side. Another disadvantage is that the presence of even a trace of water will adversely affect the activity of the potassium salt catalysts, and thus result in low conversion. Generally according to this method, the conversion of 2-pyrrolidone is between 47% and 62%, and the selectivity is about 90%. Moreover, in the case where the conversion is increased, non-volatile polymer residues are likely to be produced, resulting in difficulty of separation.

To increase the yield of NVP and decrease the formation of polymer residues, in U.S. Pat. No. 4,410,726, it is disclosed that polyoxyalkylenes (e.g. crown ether) having a molecular weight less than 2000 serving as co-catalysts are added in the vinylation reaction to increase the selectivity of NVP and the reaction rate. The yield is elevated to 70% and the selectivity is 94% under proper reaction conditions. However, a vast amount of polyoxyalkylene, usually 2 to 4 times the amount of KOH catalyst used has to be added according to this method. This kind of co-catalyst is not only very expensive but also unable to completely inhibit the formation of the polymer residues. The yield of polymer residues remains 4.5% to 6.5%, and still causes difficulty in separation during the subsequent processes. In addition, the catalyst described in U.S. Pat. No. 4,410,726 tends to be affected by water, resulting in a low NVP yield. The yield is only 70% even when the co-catalyst is added. The unavoidable polymer residues necessitate two distillation towers to separate the NVP from the raw material, 2-pyrrolidone and by-products.

SUMMARY OF THE INVENTION

It is therefore an object of the present invention to provide ether oligomers or diols having more than 4 carbon atoms serving as co-catalysts to increase the NVP yield and decrease the production of by-products. Under the catalyzation of alkali metal salts, the vinylation of 2-pyrrolidone with acetylene is accelerated, and at a vinylation temperature of 100°–200° C., a reaction pressure of 7.5–30 atm and a reaction time period of 3–20 hours, NVP is obtained with a yield over 90% and no polymer residues are formed.

An aspect of the present invention is to provide hydroxy end-capped ether oligomers having a molecular weight less than 1000 or diols as co-catalysts in the vinylation reation so that 2-pyrrolidone potasssium salt catalysts are enclosed by the ether oligomers during reactions and the interaction between OH group and potassium salt catalysts increases the activity of potassium salt catalysts, and thus accelerating the vinylation. Simultaneously the co-catalysts effectively separate water from the potassium salts, thus avoiding the deactivation of the catalysts.

More specifically, an aspect of the present invention is that the ether oligomers as co-catalysts are added in a small amount, preferably 0.5–3 wt %, and the amount of alkali metals used is also small, 0.5–3 wt % is sufficient.

Another aspect of the method of the present invention is no special treatment is needed for the removal of water in the first stage because the co-catalysts used in the invention can protect the potassium salt catalysts, and the catalysts are highly active even when a trace of water is present. Therefore, in the first stage, reacting under reflux at a temperature between 90° C. and 120° C. for a time period of 0.5–1.5 hours is sufficient to remove the produced water. And even when the water content of the raw material, 2-pyrrolidone, is as high as 500 ppm, the final yield of NVP remains over 90%. In contrast, reactions described in the above patents require special water-removing treatments, and the yields of NVP in the second stage are below 50%, if the water produced in the first stage is not completely removed.

Another aspect of the present invention is that the addition of co-catalysts not only accelerates the reaction rate but also increases the selectivity of the products. It is known from the assays of the products that NVP is the only product and no polymer residues are produced. Due to the 3-dimensional protection afforded to potassium salt catalysts by the co-catalysts, water molecules are not able to cause the open-ring reaction of 2-pyrrolidone, and the reaction is conducted under low reaction temperature, no polymer residues are produced and only one distillation tower is needed for the separation of NVP from 2-pyrrolidone in the second stage. Therefore the present invention achives low cost and high commercial profitability.

According to the present invention, vinylation of 2-pyrrolidone with acetylene produces the final product, NVP in high yields and the reaction rate is fast. The yield of NVP achives 90.5% when the reaction is proceeded for 5 hours and 97% for 10 hours.

Referring to Table 1, there is shown a comparison of the present invention and the prior art. It is evident from Table 1 that the acetylene reaction pressure of the present invention is much lower, the reaction rate is two times that of the prior art and the yield of NVP is over 10% higher than that of the prior art.

TABLE 1

|  | present invention | U.S. 4,410,726 |
|---|---|---|
| raw material limitation | water content of 2-pyrrolidone <500 ppm | water content of 2-pyrrolidone <10 ppm |
| reactor | autoclave | autoclave |
| pressure | total pressure = 10 atm ($N_2$:acetylene = 1:1) (pressure-resistance of reactor = 100 atm) | partial pressure of acetylene = 10 atm total pressure = 20 atm (pressure-resistance of reactor = 200 atm) |
| catalyst | KOH, 1.5 wt % | KOH, 1.0 wt % |
| co-catalyst | ether oligomers, 1 wt % | crown ether, 4 wt % |
| reaction temperature | 150° C. | 150° C. |
| NVP yield | 90.5%(5 hours) | 78.6%(10 hours) |
| advantage | co-catalyst accelerates reaction rate and increase the NVP yield |  |
| disadvantage |  | water contained in raw material tends to decrease the NVP yield |

Co-catalysts used in the present invention are ether oligomers having a molecular weight less than 1000, preferably, polytetramethylene ethylene glycol (PTMEG) and 1,4-BUTANEDIOL.

DETAILED DESCRIPTION OF THE INVENTION

The examples which follow illustrate the method according to the present invention without implying any limitations to the scope of the invention. In these examples, the first step reaction is carried out in a four-necked reaction flask (500 ml). 2-pyrrolidone and KOH are reacted under reflux at a temperature of 90°–120° C. for a time period of 0.5–3.0 hours, preferably 1–2 hours while purging with $N_2$ and evacuating to remove water. After the synthesis of 2-pyrrolidone potassium salt catalysts has been completed, the resultant mixture is poured into an autoclave and further reacted with a mixed gas of $N_2$/acetylene (50/50). The vinylation reaction is carried out at 100°–200° C., preferably 140°–160° C., at a total pressure of 7.5–30 atm, preferably 10–20 atm. The amount of the catalyst KOH is 0.25–8 wt %, preferably 0.5–3 wt %, based on the amount of the total reactants, and the amount of co-catalyst is 0.25–6 wt %, preferably 0.5–2 wt % based on the total reactants. The reaction time period is 3–12 hours. The product is collected after condensation, and a portion of the collected product is used to quantify the compositions of the product by a Shimadze GC-14A gas chromatograph using HP-FFAP (0.53 mm×30 m capillary column) as separation column and FID detector.

Conversion and the yield of NVP in the following examples are calculated by following equations:

$$\text{Conversion(mole \%)} = \frac{\text{moles of 2-}P \text{ before reaction} - \text{moles of 2-}P \text{ after reaction}}{\text{moles of 2-}P \text{ before reaction}} \times 100\% \quad (1)$$

$$\text{Yield of } NVP \text{(mole \%)} = \frac{\text{moles of } NVP}{\text{moles of 2-}P \text{ before reaction}} \times 100\% \quad (2)$$

EXAMPLE 1

400 g of 2-P, 7.2 g of 85% KOH (1.5 wt %) and 4.0 g of PTMEG (1 wt % ) as co-catalyst were added to a four-necked reaction flask fitted with a reflux device and stirred at 200 rpm for 30 minutes. The mixture was refluxed under 10 torr at 115°–120° C. for 1 hour while $N_2$ is introduced into the flask at every 10 minute interval to remove the water produced. After the dehydration, the reaction temperature was lowered and the synthesized potassium salt catalyst and 2-P were poured into an autoclave. The whole system was purged again by $N_2$ and then a mixed gas of acetylene/$N_2$ (50/50) was introduced and subjected to vinylation at a temperature of 150° C. and under a controlled pressure of 150 psig. Products were collected from sampling valve at every 1 hour and assayed by gas chromatograph. Table 2 shows the NVP yield for each example within a time period of 10 hours. It is known from Table 2 that the NVP yield in the present invention reaches 90% after 5 hours and is 30% higher than those of the examples without the addition of co-catalysts.

EXAMPLE 2

The same procedures as in example 1 were repeated except that 4.0 g of 1,4-butanediol was used as co-catalyst. Under the same operation conditions, the yield of NVP approaches 80% after 5 hours as shown in table 2.

COMPARATIVE EXAMPLE 1

The same procedures as in example 1 were repeated except that no co-catalyst was added. Under the same operation conditions, the yield of NVP is only 52.1% after 5 hours and less than 70% after 10 hours.

TABLE 2

|  | example 1 | example 2 | comparative example 1 |
|---|---|---|---|
| catalyst amount(wt %) | 1.5 | 1.5 | 1.5 |
| co-catalyst | PTMEG | 1,4-BDO | — |
| co-catalyst amount(wt %) | 1 | 1 | — |
| NVP yield(%) |  |  |  |
| 1 hr | 38.6 | 37.7 | 30.1 |
| 2 hr | 50.7 | 46.4 | 31.7 |
| 3 hr | 71.5 | 62.1 | 39.7 |
| 4 hr | 83.4 | 77.2 | 47.2 |

TABLE 2-continued

|  | example 1 | example 2 | comparative example 1 |
| --- | --- | --- | --- |
| 5 hr | 90.5 | 79.7 | 52.1 |
| 6 hr | 93.5 | 82.4 | — |
| 7 hr | 96.3 | 86.0 | 59.6 |
| 8 hr | 96.8 | 86.5 | 62.4 |
| 9 hr | 96.9 | 89.6 | 64.6 |
| 10 hr | 95.3 | 88.5 | 67.5 |

*catalyst = KOH, reflux = 115° C., 1 hr
reaction condition = 150° C., 150 psig

EXAMPLES 3–7

The same procedures as in example 1 were repeated except that vinylations were conducted under different pressures and at different temperatures. Table 3 indicates the yields of NVP in these examples after 10 hours.

TABLE 3

|  | Ex. 3 | Ex. 4 | Ex. 5 | Ex. 6 | Ex. 7 |
| --- | --- | --- | --- | --- | --- |
| co-catalyst | PTMEG | PTMEG | PTMEG | PTMEG | PTMEG |
| molecular-weight | 500 | 1000 | 500 | 1000 | 150 |
| amount of co-catalyst (wt %) | 1 | 1 | 1 | 1 | 1 |
| temperature (°C.) | 140 | 150 | 160 | 160 | 150 |
| total-pressure (psig) | 215 | 215 | 215 | 150 | 100 |
| ($N_2$: acetylene = 1:1) |  |  |  |  |  |
| NVP yield(mole %) | 85.6 | 92.5 | 196.1 | 83.3 | 70.1 |

EXAMPLE 8–10

The same procedures were repeated as in example 1 and under the state reaction conditions except that co-catalyst was added in different amounts. Table 4 indicates the NVP yields in these different examples after 10 hours.

TABLE 4

|  | co-catalyst | co-catalyst amount (wt %) | NVP yield (%) |
| --- | --- | --- | --- |
| example 8 | PTMEG | 2 | 88.8 |
| example 9 | PTMEG | 4 | 88.1 |
| example 10 | PTMEG | 6 | 83.5 |

EXAMPLE 11

188 g of 2-P, 3.78 g of t-potassium butoxide (2 wt %), and 1.92 g (1 wt %) of PTMEG having a molecular weight of 500 were mixed in an autoclave (300 ml). After purging by $N_2$, the autoclave is heated to 150° C. in $N_2$, and a mixed gas ($N_2$:acetylene=1:1) was introduced into the reactor and reacted under a controlled total pressure of 150 psig. Products were collected from the sampling valve at every 1 hour and assayed by gas chromatograph. The NVP yields within 10 hours are indicated in Table 5. According to Table 5, it is evident that the present invention achives 69% of NVP yield after 5 hours and 29% higher than that of an example without the addition of co-catalyst.

COMPARATIVE EXAMPLE 2

The same procedures as in example 11 were repeated and under the same reaction conditions except that no co-catalyst was added. Table 5 indicates the NVP yield is only 40% after 5 hours and less than 53% after 10 hours in this example.

TABLE 5

|  | example 11 | comparative example 2 |
| --- | --- | --- |
| catalyst amount (wt %) | 2 | 2 |
| co-catalyst | PTMEG | — |
| co-catalyst amount (wt %) | 1 | — |
| NVP yield (%) |  |  |
| 1 hr | 24.5 | 16.7 |
| 2 hr | 35.6 | 22.9 |
| 3 hr | 50.7 | 31.1 |
| 4 hr | — | 36.3 |
| 5 hr | 69.4 | 40.2 |
| 6 hr | — | 43.4 |
| 7 hr | 80.7 | 46.7 |
| 8 hr | — | 48.7 |
| 9 hr | 85.1 | 51.0 |
| 10 hr | 86.0 | 52.0 |

*Catalyst = t-potassium butoxide
Reaction conditions = 150° C., 150 psig

What is claimed is:

1. A method for the production of N-vinyl-2-pyrrolidone by vinylation, comprising the following steps:
   (a) reacting 2-pyrrolidone with acetylene in the presence of hydroxy end-capped ether oligomers having a molecular weight of less than 1000 or linear diols having at least 4 carbon atoms as co-catalysts under the catalyzation of alkali metal salts at a temperature ranging from 100° C. to 200° C. and a pressure between 7.5 and 30 atmosphere pressure; and
   (b) separating the N-vinyl-2-pyrrolidone;
   wherein the improvement is characterized in that:
   (i) said ether oligomers having the formula of $HO(CH_2CH_2CH_2CH_2O)_nH$, where n=1~14; and
   (ii) said linear diols having the formula of $HO-(CH_2)_n-OH$, where $n \geq 4$.

2. The method as claimed in claim 1, wherein said ether oligomers are polytetramethylene ethylene glycol (PTMEG) with a molecular weight of 100–1000 and are added in an amount of 0.25–6 wt % based on the amount of the 2-pyrrolidone.

3. The method as claimed in claim 2, wherein said PTMEG is added in an amount of 0.5–2 wt %.

4. The method as claimed in claim 1, wherein said alkali metal salts are selected from the group consisting of organic salts or inorganic salts of potassium, sodium, or cesium and are added in an amount of 0.25–8 wt % based on the amount of the 2-pyrrolidone.

5. The method as claimed in claim 4, wherein said alkali metal salts are added in an amount of 0.5–3 wt %.

6. The method as claimed in claim 1, wherein said vinylation is conducted between 1400° C. and 1600° C., and at a pressure ranging from 10 to 20 atmosphere pressure.

7. The method as claimed in claim 1, wherein said co-catalysts are linear diols having at least four carbon atoms.

8. The method as claimed in claim 1, wherein said co-catalysts are hydroxy end-capped ether oilgomers having a molecular weight of less than 1,000.

9. The method as claimed in claim 1, wherein said co-catalyst is 1,4-butanediol.

* * * * *